United States Patent [19]

Reed et al.

[11] Patent Number: 4,769,593
[45] Date of Patent: Sep. 6, 1988

[54] METHOD AND APPARATUS FOR MEASUREMENT OF STEAM QUALITY

[75] Inventors: Philip W. Reed; John D. Alexander, both of Ponca City, Okla.

[73] Assignee: Conoco Inc., Ponca City, Okla.

[21] Appl. No.: 873,013

[22] Filed: Jun. 10, 1986

[51] Int. Cl.$^4$ ............................................. G01K 17/06
[52] U.S. Cl. .................................... 324/61 R; 73/29; 374/42
[58] Field of Search ........... 324/61 R, 61 QS, 61 QL; 73/29, 861.04; 374/42

[56] References Cited

U.S. PATENT DOCUMENTS

| | | | |
|---|---|---|---|
| 2,718,619 | 9/1955 | Whittier | 324/61 QL |
| 3,046,479 | 7/1962 | Mead et al. | 324/61 |
| 3,090,004 | 5/1963 | Breen et al. | 324/61 |
| 3,300,716 | 1/1967 | Engert | 324/61 QL |
| 3,995,488 | 12/1976 | Crawley | 324/61 R |
| 4,034,597 | 7/1977 | Fredriksson | 73/29 |
| 4,429,273 | 1/1984 | Mazzagatti | 324/61 R |
| 4,542,993 | 9/1985 | Mimms et al. | 374/42 |
| 4,547,078 | 10/1985 | Long et al. | 374/42 |

OTHER PUBLICATIONS

Bleakley, W. B., "How to Find Steam Quality", pp. 44-45 (1965).
Gregory, G. A. and L. Mattar, "An In-Situ Volume Fraction Sensor for Two-Phase Flows of Non-Electrolytes", pp. 48-52, Apr.-Jun. (1973).
Anderson, J. L., S. E. Falke, and D. N. Clum, "A Microprocessor-Based Steam Generator Quality Controller", (1984).
Harris, R. K., "Microprocessor System Optimizes Steam Generator/EOR Operation", pp. 39-46, Mar. (1986).
Lundstrom, J., "Capacitance-Based Moisture Computer", pp. 46-47, May (1986).

Primary Examiner—A. D. Pellinen
Assistant Examiner—Jeffrey A. Gaffin
Attorney, Agent, or Firm—Richard K. Thomson

[57] ABSTRACT

A method and apparatus for directly measuring steam quality in-line. A variable frequency capacitance cell receives a hybrid stream (one having both liquid and vapor phases). The resultant frequency of the electrical circuit of which the capacitance cell is an element, varies with the dielectric constant of the capacitance cell (i.e., the water vapor concentration in the cell). The resultant frequency of the cell is preferably beat with a reference frequency that is within about 15 MHz from the resultant frequency to facilitate measurement.

19 Claims, 1 Drawing Sheet

METHOD AND APPARATUS FOR MEASUREMENT OF STEAM QUALITY

BACKGROUND AND SUMMARY OF THE INVENTION

The present invention is directed to a method and apparatus for measuring steam quality of a hybrid stream having both vapor and liquid phases directly in the flow line.

One of the least expensive and potentially most cost effective methods of enhanced oil recovery (EOR) involves the injection of high pressure steam to heat the oil reducing its viscosity and to thereby displace the oil from the pore volume of the oil-bearing formation entrapping it. In order to properly estimate the amount of oil that can be recovered through EOR, one must know the volume and the quality of steam in order to calculate the quantity of heat input into the reservoir.

In the steam injection process, single path steam generators are typically used. Dry superheated steam (i.e., quality of 100%) is not used in this process because of the potentially harmful effects to the equipment. The impurities in the water will not remain in solution in dry steam and build up forming scale in the steam generator and associated feed lines. Scale buildup insulates the tubes of the steam generator preventing proper heat dissipation leading to overheating and possible rupture at high pressures. Steam having a quality of 80% (i.e., 80% by weight vapor, 20% liquid) has been shown to be optimum, protecting equipment from scale buildup while providing an acceptable rate of heat input. Without an adequate in-line means of determining steam quality, operators will typically run their systems at lower quality steam output to protect their steam generators. This results in lesser quantities of heat being input to the reservoir resulting in less oil being recovered than calculated and potentially jeopardizing the economics of the EOR process. Further, with a fluctuating steam quality, the operating efficiency of the steam generator remains an unknown, although the operating life will certainly be less than it could be were a steady state steam quality to be maintained.

One of the most significant problems associated with steam injection for EOR applications is the absence of any means to directly measure steam quality in the flow line. Currently, one of the most widely used processes involves titration of an extracted liquid sample to compare the percentage level of impurities in the input water used to formuate the steam. This process is time consuming and inhibits accurate steam quality control. Further, if a single steam generator is providing steam to a plurality of injection wells by means of stream splitting using conventional piping such as a pipe tee (a process for which it can be demonstrated that the qualities of the resultant streams are not uniform), the titration process cannot be used to determine steam quality.

Orifice meters can be used to estimate steam quality if flow rate is known or to estimate flow rate if quality is known. Steam flow rate is related to steam quality by the following formula:

$$M = a \cdot b (f1)(f2) \sqrt{pP}$$

where:

M = mass flow rate of steam in pounds per hour a = basic orifice factor, a constant for a particular pipe and orifice diameter b = an expansion factor, also a constant for a particular system f1 = an empirical correction factor for steam quality f2 = correction factor to account for expansion through orifice plate p = differential pressure across the orifice P = absolute flow line pressure The reason orifice meters produce estimates rather than accurate measurements is two fold. First, the presence of significant amounts of liquid (i.e., exceeding 5% by weight) in the flow stream make it impossible to obtain accurate readings of the differential pressure p. A best guess average is generally used. Second, the estimate is derived through an iterative process in which various of the factors are derived through interpolation and then adjustments are made to the results to achieve the desired mass balance on the two sides of the equation. Such an approximation is not entirely satisfactory.

The method and apparatus of the present invention enable a direct real-time measurement of steam quality to be made. The apparatus of the present invention utilizes an in-line, high-frequency (e.g., 40 MHz) capacitance cell. The capacitance of the cell is a function of the dielectric constant of the material within the cell which varies with the percentage of liquid water (i.e., with the steam quality). The change in capacitance of the cell alters the resonant (or resultant) frequency of the electrical circuit of which it is a part. It is preferred that the resultant frequency from the cell be mixed with a reference frequency to produce a beat frequency. This enables more accurate readngs to be made and less sophisticated equipment to be used to measure the capacitance changes resulting from the changes in steam quality.

Various other features, advantages and characteristics of the present invention will become apparent after a reading of the following specification.

DETAILED DESCRIPTION OF THE PREFERRED EMBODIMENTS

Prior to describing the test apparatus used to demonstrate the principles of the present invention, it should be noted that this was, indeed, a test facility. Existing steam generation equipment which was normally used to produce steam for heating purposes, was used as a matter of convenience and an available capacitance cell utilized even though its instrumentation package was not state-of-the-art. Although additional work may be warranted to optimize the system, applicants have sufficiently demonstrated the viability of the method and applicability of the apparatus to justify the present application.

Figure 1:
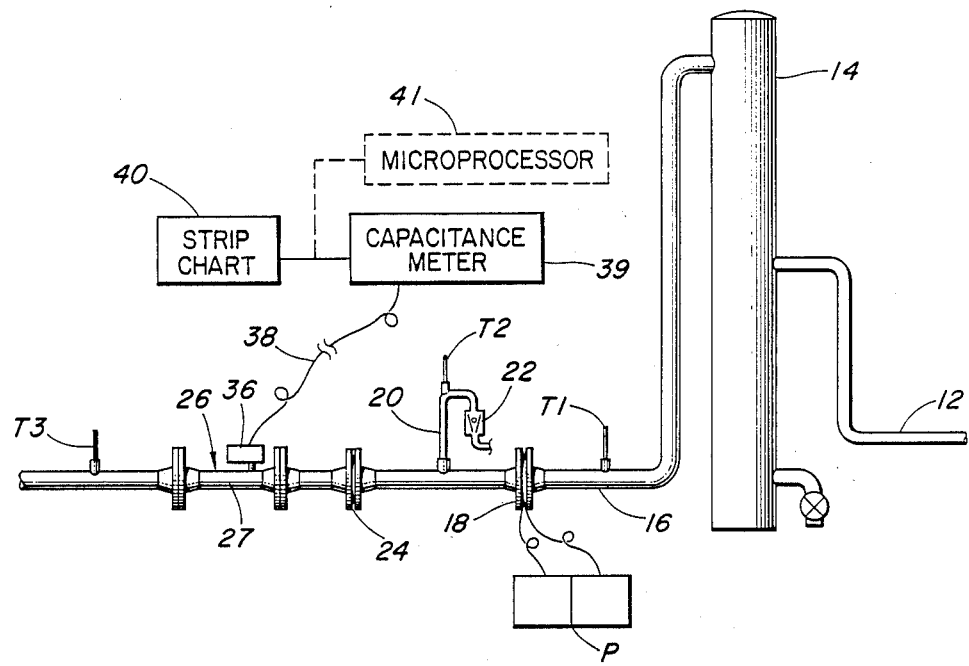
FIG. 1 is a schematic side view depicting the test apparatus that was utilized to prove the theory of operation of the present invention.

As seen in FIG. 1, the test apparatus comprises an in-feed flow line 12, feeding steam from a generator (not shown) to a separator 14. As noted above, the steam generator was designed to produce steam for heating purposes and therefore provided low prssure steam. The steam passing through the test equipment was in about the 3 psig range. The entire flow line was insulated for these tests to reduce heat loss. Nonetheless, since there was a considerable distance between the steam generator and the remaining test apparatus, separator 14 was necessary to eliminate any condensate from the steam. This separator is a conventional gas/liquid separator employing internal baffles and a metal mesh mist extractor at the gas outlet. Flow line 16 received 100% quality (dry) steam so that the percent liquid added (and hence, the quality) could be controlled.

Flow line 16 fed the dry steam to an orifice meter 18. A first thermocouple, T1, and pressure transmitters, P, interconnected to the test apparatus through the orifice meter 18, were used to measure the input temperature and pressure of the dry steam. Orifice meter 18 contains two pressure transmitters, one measuring the differential pressure at the orifice, one measuring the static pressure immediately upstream of the orifice. Immediately downstream of the orifice meter 18 was a water injection station 20. A second thermocouple, T2, was used to measure the input temperature of the water and a variable area flow meter 22 used to measure the volume flow rate of the water being input. The water was injected into the flow line using a spray injection nozzle (not shown). Meter 22 was precalibrated with the nozzle connected to verify flow rate.

Figure 2:
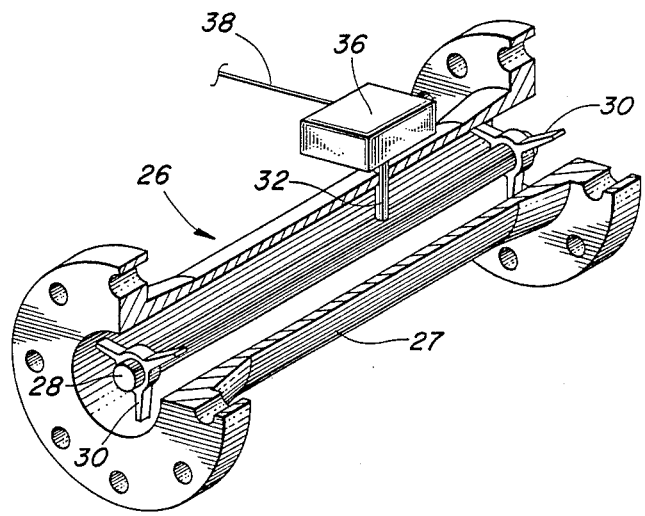
FIG. 2 is an enlarged perspective with parts broken away, showing the details of the capacitance cell used in the test apparatus.

The hybrid stream, now containing both a liquid phase and a gas phase, was fed through mixing orifice 24 to homogenize the water distribution as a mist within the steam vapor. The homogenized hybrid stream was then fed into capacitance cell 26. The capacitance cell 26 was a center rod, spool-type cell and comprised a flanged spool-shaped pipe section 27. The section was 14" long and the pipe 3" in diameter. The details of the capacitance cell are best seen in FIG. 2. Center rod 28, forming one "plate" of the capacitor, is held in a position centered within spool 27 by a pair of plastic spiders 30. A solid metallic rod 32 was threaded into center rod 28 and formed the electrical contact between electrical box 36 and the capacitance cell 26. The internal surface of spool 27, which forms the other capacitor "plate", and the external surfaces of center rod 28 and connector rod 32 were coated with a corrosion resistant, electrically insulative and thermally stable material; for examle, polyphenylene sulfide. Spiders 30 may be made of the same material. A third thermocouple, T3, downstream of the capacitance cell 26 was used to measure the temperature of the hybrid stream.

The electrical box 36 includes a transistor and an inductance (not shown) which together with the capacitance cell 26 form a circuit portion for which the frequency changes as the capacitance of the cell changes. This varying frequency is known as the resonant or resultant frequency of the capacitance cell 26. Such a change in capacitance is brought about by a change in the dielectric constant of the material withi cell 26 which fluctuates significantly as the water content changes (the dielectric constant for water is 81 as compared to about 2 for gas, 4 for paper, 6 for wood, and 8 for glass). Cable 38 connects electrical box 36 to a control panel containing additional electronic components including a strip chart 40 for recording frequency output.

A high frequency of about 40 megahertz (MHz) was selected for use with capacitance cell 26. It will be understood, however, that other high frequencies will work and, indeed, any frequency exceeding about 20 MHz should work, with a range of between 25 and 70 MHz being preferred. By selecting a frequency above about 20 MHz, the effects of leakage resistance are minimized and the frequency dependence of the dielectric constant (dielectric dispersion) effectively eliminated.

This resultant frequency was mixed in capacitance meter 39 with a reference frequency from a crystal oscillator having a frequency of 50 MHz to produce a beat frequency on the order of 10 MHz. By doing so, the changes in frequency resulting from capacitance changes in the meter form a greater percentage of the signal being measured (i.e., the changes are more easily read) and can be measured with less expensive equipment. Again, the reference frequency chosen is exemplary. The resultant frequency can be beat with any frequency but to achieve the above-noted advantages the frequency chosen should be within about 15 MHz and, preferably, separated by about 10 MHz. Further, the reference frequency can be above or below the resultant frequency but should be selected to be consistently above or below (i.e., the reference signal frequency should not be so close to the variable resultant frequency that the latter would vary both above and below the former, complicating analysis).

The output signal from the capacitance meter 39 (i.e., the best frequency) was recorded on a strip chart 40 and changes in quality resulting from changes in water flow rates produced well defined, easily readable output variations.

Four separate sets of tests were run on four different days, roughly each a week apart. The steam was fed into flow line 12. The system was allowed to reach equilibrium (with the water shut off) for 30 minutes, readings taken and then water was added in increasing amounts. Each value for water flow rate, respresnts the average of 3 readings taken at one minute intervals.

In order to calibrate the meter, the total enthalpy of the hybrid stream was calculated using the temperature readings from thermocouples T1 and T2 and the pressure readings of pressure transmitters P along with the flow rates measured by meter 22. The volume flow rates of vapor and liquid phases were divided based on known enthalpy of the system, and steam quality then determined. The resultant qualities and the meter readings for the four separate runs are shown in Table I.

TABLE I

| RUN NUMBER | QUALITY (%) METER READING (MHz) | | | | | | | | | | | | | |
| --- | --- | --- | --- | --- | --- | --- | --- | --- | --- | --- | --- | --- | --- | --- |
| | 7.7 | 9.5 | 10.1 | 13.1 | 17.3 | 17.8 | 18.2 | 21.3 | 39.5 | 51.8 | 58.6 | 67.8 | 80.4 | 100 |
| 1 | | | | | | | | | | 10.523 | 10.505 | 10.478 | 10.446 | 10.393 |
| 2 | 10.634 | | | 10.582 | | | | 10.520 | 10.475 | | | | | 10.334 |
| 3 | | 10.451 | | | 10.394 | 10.386 | | | | | | | | 10.114 |
| 4 | | | 10.631 | | | | 10.579 | | | | | | | 10.330 |

The variation in quality from 7.7 to 100% at approximately 3 psig for these tests is equivalent to a range of 87 to 100% at 1000 psia, the input pressure for normal injection. The variation exhibited in the qualities shown between runs was due in part to the desire to test the equipment over a widely varying range and, in part, to the lack of precise flow rate control for the water input. It is not fully understood why the dry steam readings for the four runs varied and several possible explanations were offered. It was concluded, however, that this problem with the data indicated a need to fine tune the equipment rather than a deficiency in the method or principles of system operation.

It should be pointed out that the capacitance meter utilized in the current testing had been successfully utilized in a high-pressure (900 psi) gas/water environment in earlier tests and, therefore, should be readily converted to use in a high-pressure EOR system. Such a capacitance meter could be used in each injection line immediately adjacent the injection point into the wellhead to measure quality of the steam as it goes into the ground. This, in conjunction with volume measurement, would provide a measure of heat input into the well, which has not been heretofore possible. It is envisioned that the capacitance meter of the type disclosed would be incorporated into an EOR system with a microprocessor 41. The steam table data would be preprogrammed into memory and then the temperature and pressure data (only one of which is necessary to compute steam quality in steady-state conditions) and the capacitance meter reading would be used to calculate steam quality. This numeric value, or percent volume water, if preferred, could appear as a digital readout and be recorded so that actual heat input could be computed. Further, a capacitance meter interconnected to a microprocessor could be positioned immediately adjacent the steam generator and could be utilized to adjust steam generator input to control quality or activate alarms, as desired. In this manner, a continuous, more precise in-line measurement of steam quality than heretofore possible could be made and used to protect the steam generator while maximizing heat input.

Various changes, alternatives and modifications will become apparent following a reading of the foregoing specification. For example, although only a center rod, spool-type capacitance cell has been shown, capacitors of other configurations (including conventional straight and curved plate varieties) could be used equally as well. In fact, it is likely that the use of a parallel dual-spiral capacitor would obviate the need for a mixing orifice. Accordingly, it is intended that all such changes, alternatives and modifications as come within the scope of the appended claims, be considered part of the present invention.

We claim:

1. A method of continuously measuring the quality of steam in a flow line containing a hybrid stream of both a gas phase and a liquid phase, said method comprising:
    providing an electrical circuit which operates at a resultant frequency exceeding 20 MHz;
    flowing said hybrid stream through an element of said electrical circuit to induce a change in capacitance within said circuit said change in capacitance producing a change in said resultant frequency of the electrical circuit;
    measuring the magnitude of the resultant frequency, said magnitude being a function of a variance in dielectric constant which is proportional to percent liquid in said hybrid stream;
    measuring the hybrid stream's temperature and pressure; calculating the steam quality of said hybrid stream.

2. The method of claim 1 wherein the resultant operating frequency preferably is in the range of from 25 to 70 MHz.

3. The method of claim 2 wherein the resultant operating frequency is most preferably about 40 MHz.

4. The method of claim 2 further comprising the step of mixing the resultant frequency with a reference frequency to produce a beat frequency.

5. The method of claim 4 wherein said reference frequency of said mixing step has a frequency that is separated from the frequency of said resultant frequency by about 10 MHz.

6. The method of claim 5 wherein the reference frequency of said mixing step is about 50 MHz.

7. The method of claim 1 further comprising the step of mixing the resultant frequency with a reference frequency to produce a beat frequency.

8. The method of claim 7 wherein the reference frequency of said mixing step is separated from the said resultant frequency by about 10 MHz.

9. Apparatus for continuously measuring the steam quality of a hybrid stream in a flow line containing both a gas phase and a liquid phase, said hybrid stream having a temperature and a pressure, said apparatus comprising:
    an electrical circuit operating at a resultant frequency exceeding 20 MHz;
    flow means for said hybrid stream passing through an element of said electrical circuit to induce a change in capacitance within said circuit which, in turn, produces a change in said resultant frequency;
    means for measuring the magnitude of said resultant frequency, said magnitude being a function of a variance in dielectric constant resulting from the fluctuation in said liquid phase;
    means for measuring the temperature or pressure of said hybrid stream;
    means for calculating the steam quality given the resultant frequency and the temperature or pressure of said hybrid stream.

10. The apparatus of claim 9 wherein said electrical circuit more preferably has a resultant operating frequency in the range from 25 to 70 MHz.

11. The apparatus of claim 10 wherein said electrical circuit most preferably has a resultant operating frequency of about 40 MHz.

12. The apparatus of claim 9 wherein said element of said electrical circuit through which said hybrid stream passes comprises a capacitance cell inserted directly in said flow line.

13. The apparatus of claim 12 wherein said capacitance cell comprises a center rod, spool-type capacitance cell.

14. The apparatus of claim 13 wherein the surfaces of the center rod and the spool of said capacitance cell are coated with a corrosion-resistant, thermally resistant and electrically insulative material.

15. The apparatus of claim 14 wherein said corrosion-resistant, thermally resistant and electrically insulative material is polyphenylene sulfide.

16. The apparatus of claim 9 further comprising means for generating a reference frequency and means for mixing said reference frequency and said resultant frequency to produce a beat frequency.

17. The apparatus of claim 16 wherein said means for generating said reference frequency comprises a crystal oscillator which produces a frequency of about 50 MHz.

18. The apparatus of claim 9 further comprising means for mixing said hybrid stream to homogenize the liquid phase within the gas phase of said hybrid stream, upstream of the element in said electrical circuit through which said hybrid stream flows.

19. The apparatus of claim 18 wherein said mixing means comprises a mixing orifice situated in said flow line immediately upstream of said element in said electrical circuit.

* * * * *